US00PP36859P2

(12) United States Plant Patent
Hansoti

(10) Patent No.: US PP36,859 P2
(45) Date of Patent: Jul. 22, 2025

(54) ***SANSEVIERIA* PLANT NAMED 'HANSOTI56'**

(50) Latin Name: *Sansevieria trifasciata*
Varietal Denomination: HANSOTI56

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,646

(22) Filed: Dec. 23, 2024

(51) Int. Cl.
*A01H 6/12* (2018.01)
*A01H 5/12* (2018.01)

(52) U.S. Cl.
USPC ..... Plt./382

(58) Field of Classification Search
USPC ..... Plt./373, 382
See application file for complete search history.

(56) References Cited

U.S. PATENT DOCUMENTS

PP30,342 P2 * 4/2019 Hansoti ..... A01H 5/12
Plt./382

* cited by examiner

*Primary Examiner* — Karen M Redden

(57) ABSTRACT

A new and distinct cultivar of *Sansevieria* plant named 'HANSOTI56' is disclosed, characterized highly variegated foliage with an overall bright creamy yellow coloration of the leaf and a contrasting, broad central greyish-green band. The new cultivar can be classified in the Compact *Sansevieria* Group type *Sansevieria* and reaches about 25 to 30 cm in height at maturity, making it a shorter cultivar in this group. Plants are ready to sell in about 3 to 4 months from a rooted liner, having 10 to 15 leaves. Foliage is softer, thinner and more pliable than typical in the Compact *Sansevieria* Group. The new variety is a *Sansevieria*, typically produced as an ornamental plant.

11 Drawing Sheets

Latin name of the genus and species: *Sansevieria trifasciata.*

Variety denomination: 'HANSOTI56'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI56'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI56' was discovered and selected by the inventor, Ashish Hansoti, in mid-2018, from several aberrant golden leaved mutant side-shoots arising from plants of *Sansevieria trifasciata* 'Hansoti23', now commercially called 'HiColor' (U.S. Plant Pat. No. 33,150), at a nursery in Village Vangani, District Thane, Maharashtra State in Western India.

The cultivar 'HiColor', as with many highly variegated plants, gives the occasional highly variegated or entirely albino shoot-in this case these "albino" shoots are golden colored. The inventor selected, from these highly variegated side shoots, single strong shoots with significant green leaf centers that were self-sustaining and healthy. Subsequent strict selection of appropriately colored shoots with discarding of non-standard and albino shoots gave rise to a new, highly colored yet stable cultivar now denominated as 'Hansoti56'. By mid-2019 we had the new cultivar isolated and coming true from side shoots and growing strongly (given the highly variegated nature of this new selection).

Bulking up by asexual reproduction of the new *Sansevieria* cultivar 'Hansoti56' by vegetative side shoot cuttings was performed throughout 2020, 2021 and 2022 at Village Asle, District Satara, Maharashtra State in Western India, and it was seen that the distinctive combination of characteristics of the new cultivar reproduced true to type as long as the propagation was done through side shoots (basal suckers) originating from the base of the parent plant. Thus, it can be said that the new cultivar now reproduces true to type through side shoots (basal suckers).

BRIEF SUMMARY OF THE INVENTION

The following traits have been repeatedly observed and are determined to be unique characteristics of 'HANSOTI56', which in combination distinguish this *Sansevieria* as a new and distinct cultivar:

1. Highly variegated foliage with an overall bright creamy yellow coloration of the leaf and a contrasting, broad central greyish-green band. Overall, 'Hansoti56' is one of the most brightly colored *Sansevieria* hybrids known to the inventor.
2. Bright creamy yellow marginal band of 3 to 10 mm wide, equally wide on both edges of each leaf.
3. At 25 to 30 cm plant height above pot, this is one of the smaller or shorter cultivars amongst the *Sansevieria* nominated as "Compact *Sansevieria* Group".
4. Ready to sell, 3 to 4 month (from rooted liner) old plants have 10 to 15 leaves per plant which is relatively high compared to other *Sansevieria* in the "Compact *Sansevieria* Group". This gives a more bushy, full plant compared to other *Sansevieria* in the "Compact *San-*

*sevieria* Group". As a commercial pot plant this cultivar may be grown as a two Plants per Pot (2PP) plant for even more fuller look.

5. Relatively softer, thinner, more pliable leaves. In comparison, most *Sansevieria* in the Compact Group have thicker, more stiff leaves that break more easily.

The new variety 'HANSOTI56' is considered a variety of *Sansevieria* in the group denominated as the "Compact *Sansevieria* Group". The new variety presents with numerous leaves-12 to 15 leaves per plant-when it reaches saleable size (between 3 to 4 months from rooted liner). The new variety has an erect growth habit and the entire plant can reach a height range between 25 and 35 cm. The leaves are of narrow width (from 2 to 4 cm, occasionally 5 cm wide measured at the widest part of the mature leaf under good growing conditions) and lanceolate or ensiform, erect but with a graceful curvature and a waxy texture. The blades are somewhat thick or fleshy but much less so than similar "Compact Group of *Sansevieria*". This variety also has an inverted triangle shape like most *Sansevieria* of the Compact Group.

The new variety is moderately drought tolerant and adapts well to conditions of bright light and moderate shade (exterior and interior).

The leaves show a bright variegated coloration. Each leaf has a bright border of creamy yellow. This base creamy color is near RHS Yellow 5A. This bright creamy yellow marginal band is equally broad on both sides of the leaf and varies in width from just 3 mm to 10 mm.

The central broad grey-green band, 20 to 30 mm wide, shows green colorations or striations varying from a dark green similar to RHS Green 136A to a lighter color similar to Green N138C.

Superimposed on this central green band are lighter horizontal cross-banding (typical of most broad leaved *Sansevieria* including *S. t.* 'Futura Superba', not patented) but this banding is seen only on the green central band and absent or essentially invisible on the creamy edge bands. The central green band also has random thin longitudinal streaks of yellowish cream, adding to the overall brightness of this exceptional new cultivar.

Backside or abaxial surface of the leaves are similarly colored with a wider central green band and narrower marginal creamy band. At the back of the leaf the central green band has even more streaks of yellowish cream invading the green compared to the front of the leaf. The basal $1/4^{th}$ of the back side of each leaf is more or less entirely golden yellow.

Attached color pictures are a better guide to the overall coloration than written descriptions.

PARENTAL COMPARISON

Plants of the new *Sansevieria* 'HANSOTI56' are similar to plants of the parental cultivar, however, 'HANSOTI56' differs in the characteristics described in Table I.

TABLE I

Comparison of Parental & the New variety 'Hansoti56'

| | Characteristic | Parent Cultivar 'Hansoti23' U.S. Plant Pat. 33150 | New cv 'Hansoti56' |
|---|---|---|---|
| 1. | Leaf size | 25-30 cm long and up to 6 cm wide. | 25-35 cm long but narrower - 2 to 4 cm wide. |

TABLE I-continued

Comparison of Parental & the New variety 'Hansoti56'

| | Characteristic | Parent Cultivar 'Hansoti23' U.S. Plant Pat. 33150 | New cv 'Hansoti56' |
|---|---|---|---|
| 2. | Number of leaves | 10 to 12 leaves | 12 to 15 leaves (more than parent cultivar) |
| 3. | Leaf Arrangement | Leaves held more spread out, so clump of leaves more open. | Leaves more vertically held, so a narrower clump |
| 3. | Variegation Pattern | More complex variegation with bright cream with bright green bands of various widths giving a bright, variegated appearance. | Simple variegation pattern- Bright Yellowish Cream border along leaf edge with central broad band of grey-green. |
| 4. | Border variegation | Bright green border 2 to 10 mm with obvious, prominent transverse banding. | Bright yellowish cream border 3 to 10 mm wide on both sides with no transverse banding. |
| 5. | Central Variegation | Broad green band, 3 to 4 cm wide, consisting of light and dark green streaks with bright yellow variegation on both sides of this band, between this central band and marginal bands of green. | 2 to 3 cm wide green central band with lighter green/creamy yellow streaks and subdued but obvious transverse banding. |

'Hansoti56' is therefore substantially different looking cultivar compared to the parent 'Hansoti23' except that both are of somewhat short stature, with leaves held more vertically and softer leaves than the typical *Sansevieria* of the 'Compact *Sansevieria* Group'. The variety 'Hansoti23' gave rise to the variety 'Hansoti56' (after considerable selection of appropriately colored, strong growing shoots). This *S. trifasciata* 'Hansoti23' is also part of the "Compact *Sansevieria* Group" but has broader, more complexly colored and patterned leaves.

COMMERCIAL COMPARATOR

Plants of the new *Sansevieria* 'HANSOTI56' are similar to the commercial variety *Sansevieria trifasciata* 'Gold Flame', unpatented. Plants of the new *Sansevieria* 'HANSOTI56' differ from plants of the commercial cultivar in the characteristics described in Table II.

TABLE II

Comparison of comparable variety '*S. t.* 'Gold Flame' & the new variety 'Hansoti56'

| | Characteristic | Comparable cv *S. t.* 'Gold Flame' (unpatented) | New cv 'Hansoti56' |
|---|---|---|---|
| 1. | Leaf size | 25 to 35 cm long | 25 to 35 cm long |
| 2. | Number of leaves | 6 to 8 leaves (Fewer) | 12 to 15 leaves (More leaves) |
| 3. | Variegation Pattern | Variegation pattern is very variable and changes with leaf age; mature, highly colored plants show large areas of golden yellow variegation on the leaves. Pattern is relatively random. Some transverse banding seen on top surface where the leaf is | Variegation pattern is very stable with central green band and marginal creamy yellow bands. The green central band has transverse banding on top as |

TABLE II-continued

Comparison of comparable variety '*S. t.* 'Gold Flame' & the new variety 'Hansoti56'

| | Characteristic | Comparable cv *S. t.* 'Gold Flame' (unpatented) | New cv 'Hansoti56' |
|---|---|---|---|
| | | green but seen prominently on bottom surface. | well as bottom surfaces of the leaf. |
| | Variegation Color | Under good light and nutrition, the variegation color is a deep Golden yellow | Under good light and nutrition, the variegation color is a lighter creamy yellow |
| 4. | Border variegation | 2 to 15 mm wide golden band along leaf edge which, with increasing leaf maturity, expands to eventually cover most or even all of the leaf. Backside of leaf has more distinct yellow border. | Stable border of creamy yellow 3 to 10 mm wide with no transverse banding. |
| 5. | Central Variegation | Variegation typically starts as a small marking in center of the top half of the leaf and expands, in leaves of increasing maturity, to cover most of the leaf. In older plants under high light new leaves can come out almost entirely yellow gold. | The leaf has a broad central band of green with streaks of lighter green and occasional streaks of creamy yellow within this green band. Transverse-banding (typical of *Sansevieria trifasciata*) seen on green band. |

BRIEF DESCRIPTION OF THE PHOTOGRAPHS

The accompanying photographs illustrate the overall appearance of the new *Sansevieria* cultivar 'HANSOTI56' showing the colors as true as is reasonably possible with colored reproductions of this type. Colors in the photographs may differ slightly from the color value cited in the detailed botanical description which accurately describe the color of 'HANSOTI56'.

These pictures illustrate the plant form which is the unique characteristic of 'HANSOTI56' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

FIG. 1, FIG. 2 and FIG. 3: Show a single plant, ready-to-sell size of *Sansevieria* 'Hansoti56' in a 12 cm diameter pot from various angles to illustrate leaf shape and color, leaf phyllotaxy.

Specifically, FIG. 1 is a top down view illustrating the variegation pattern and color. The relatively narrow leaves are obvious.

Figure 1:
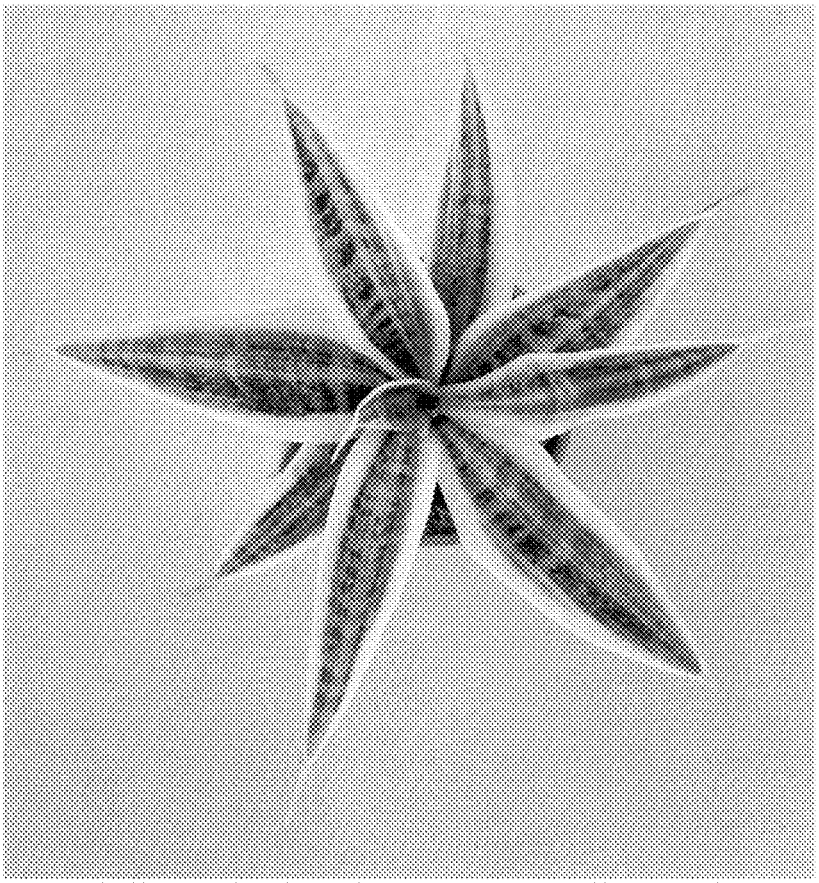
Figure 2:
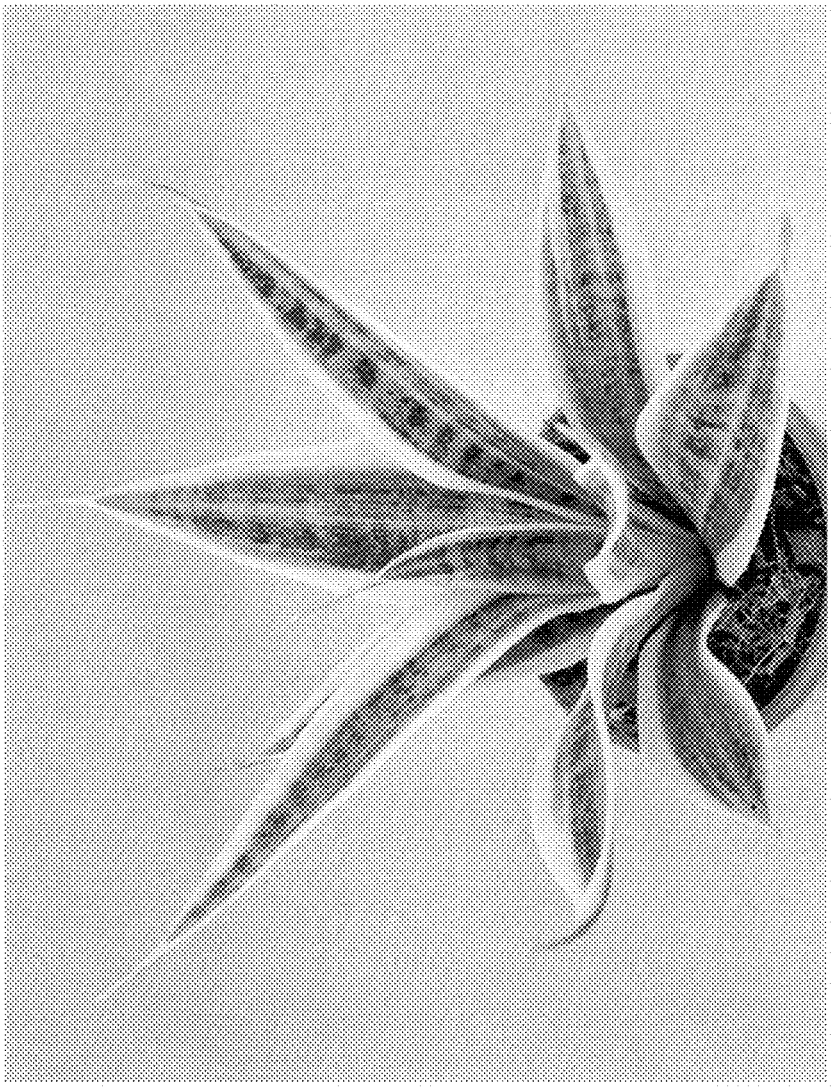
FIG. 2 is an angled view from above, also showing the variegation pattern and color.
Figure 3:
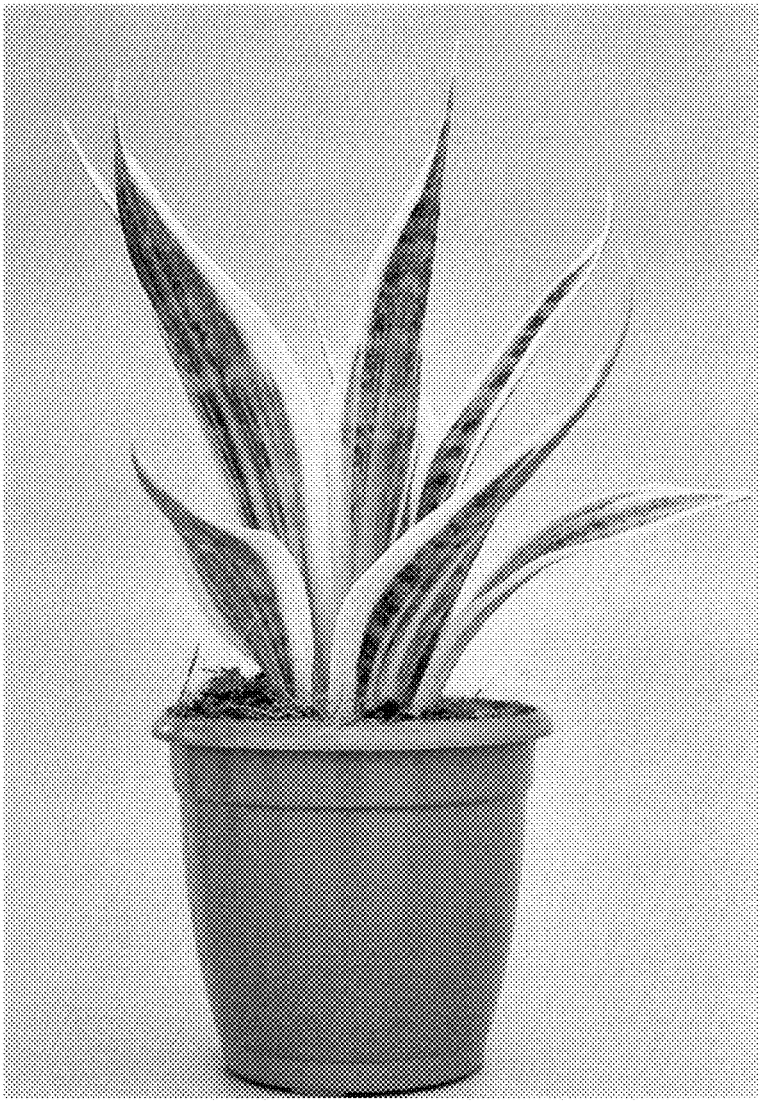
FIG. 3 is a side view, illustrating the underside of the foliage, as well as the characteristic curve of the foliage.
Figure 4:
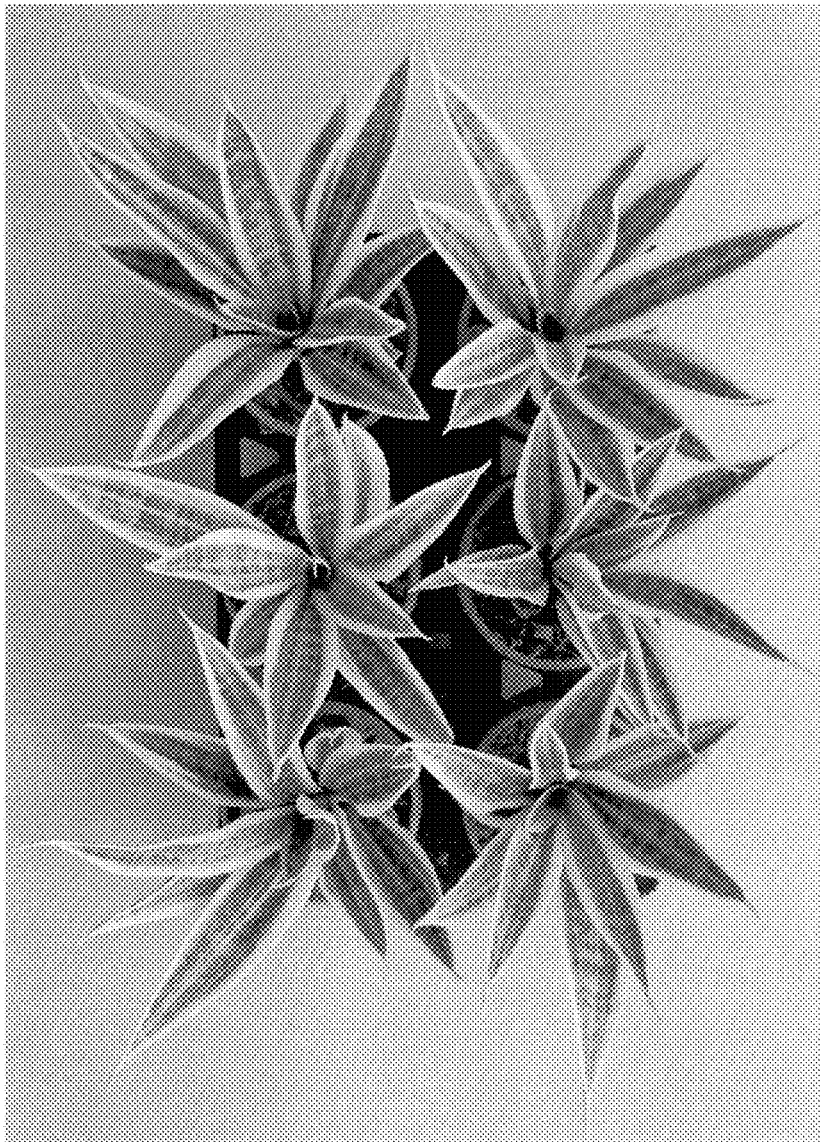
Figure 5:
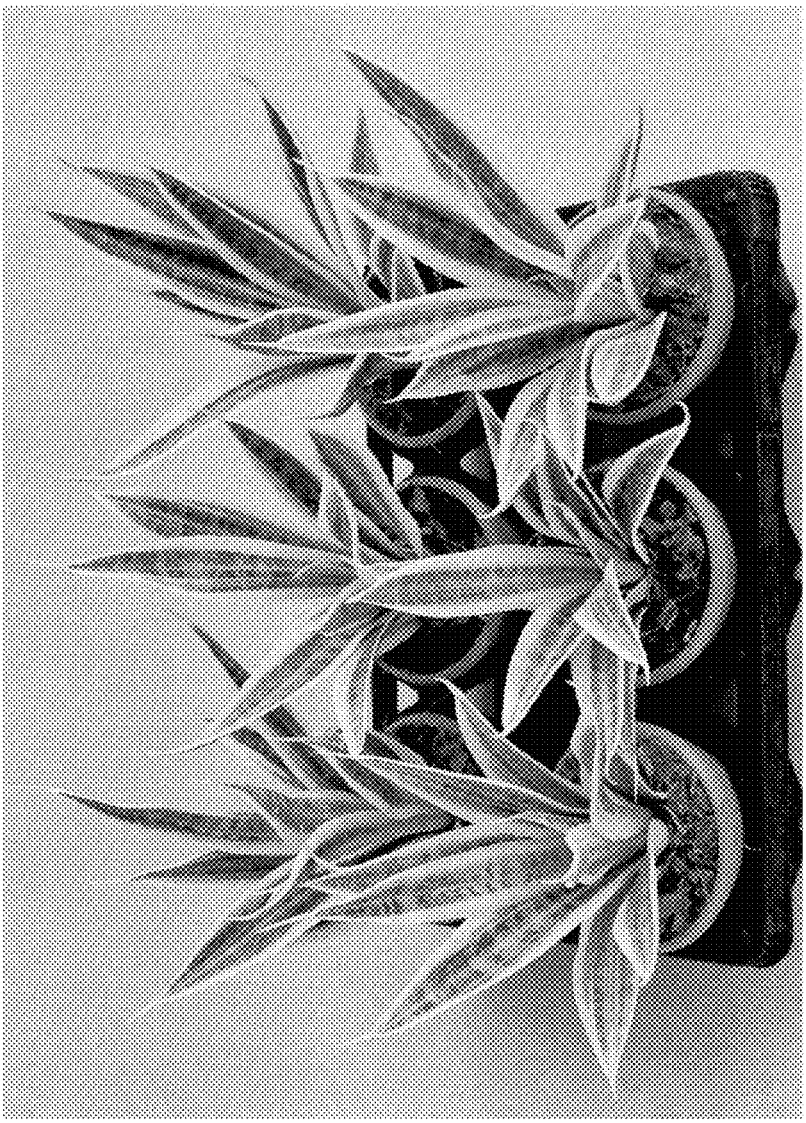
Figure 6:
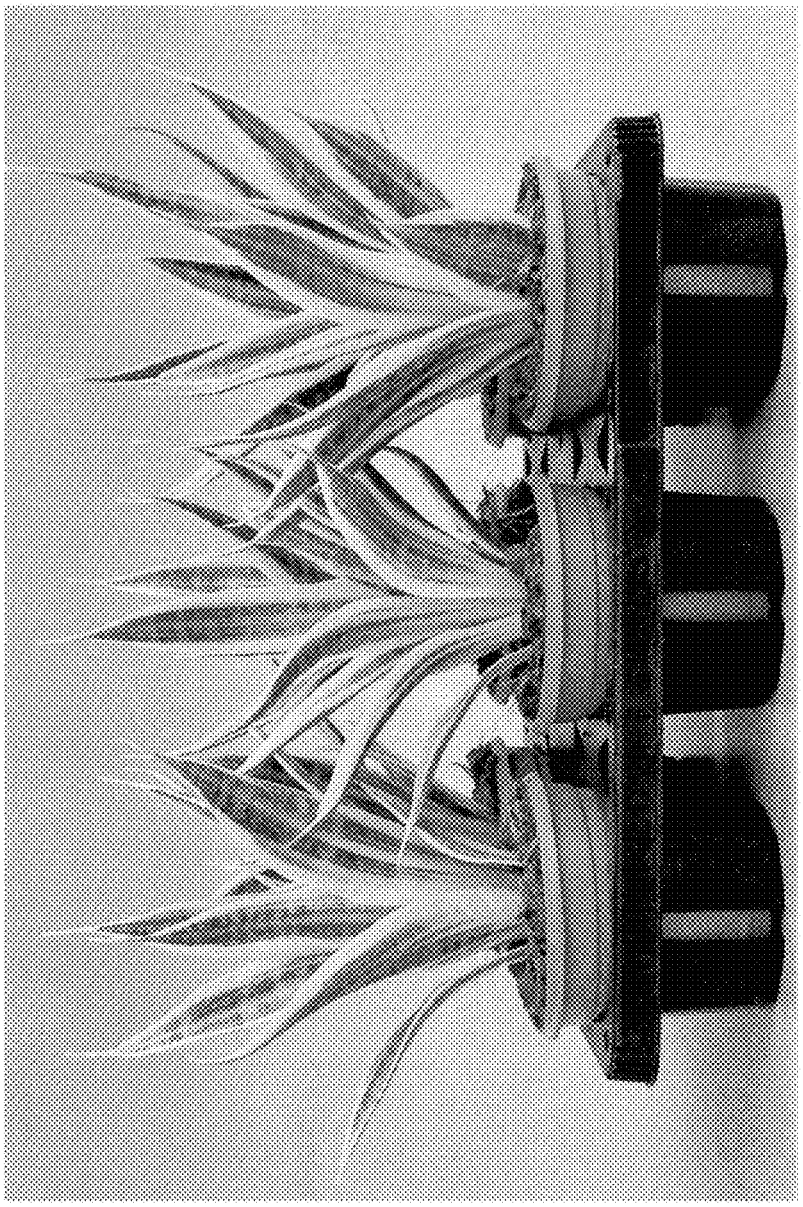

FIG. 4, FIG. 5 and FIG. 6: Show 6 plants of 'Hansoti56' in a tray, several plants together show the uniformity achieved by this cultivar in plant form, leaf shape and color as well as variegation pattern.

Figure 7:
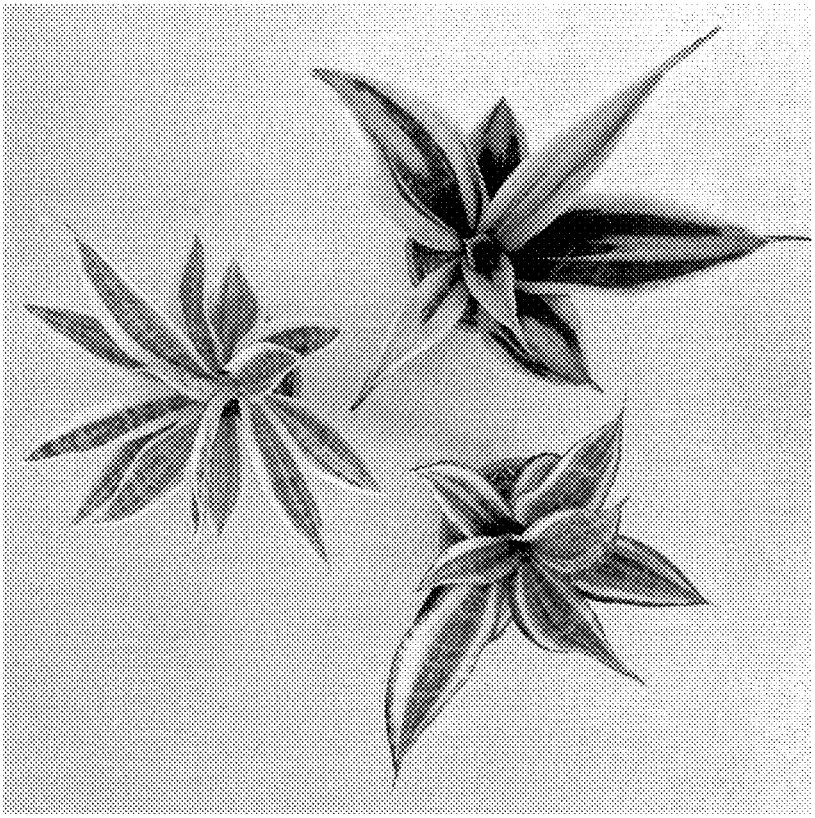
Figure 8:
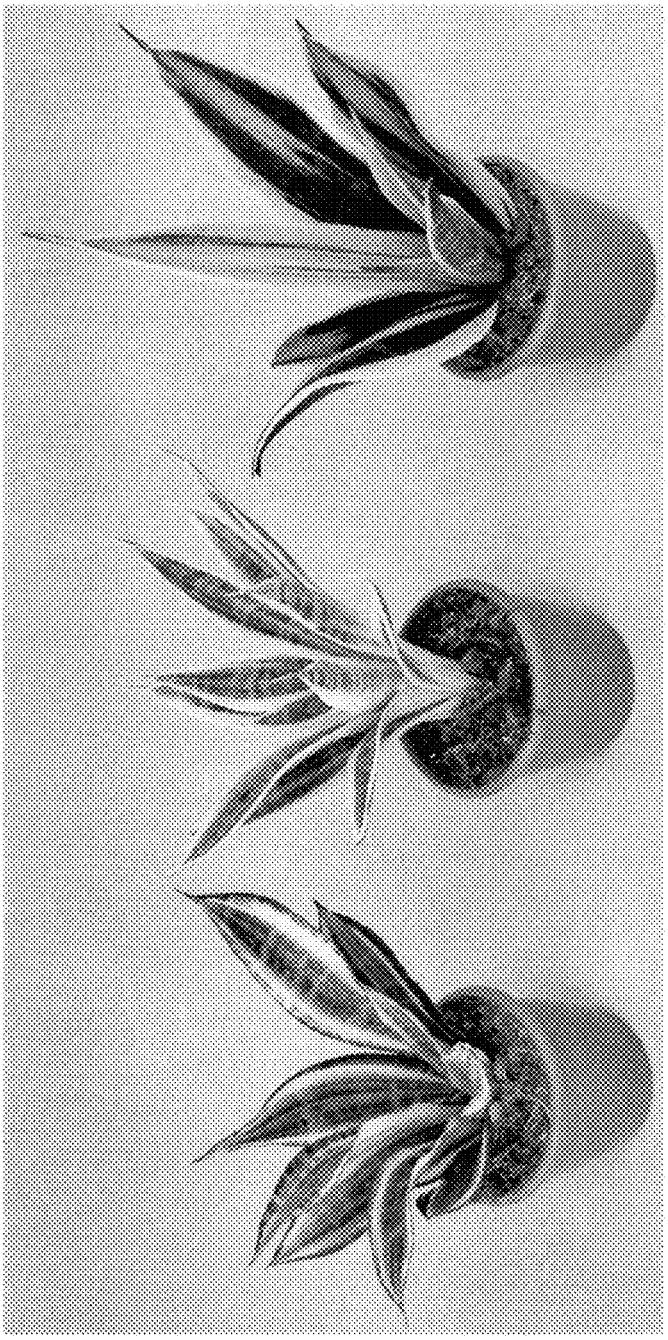
Figure 9:
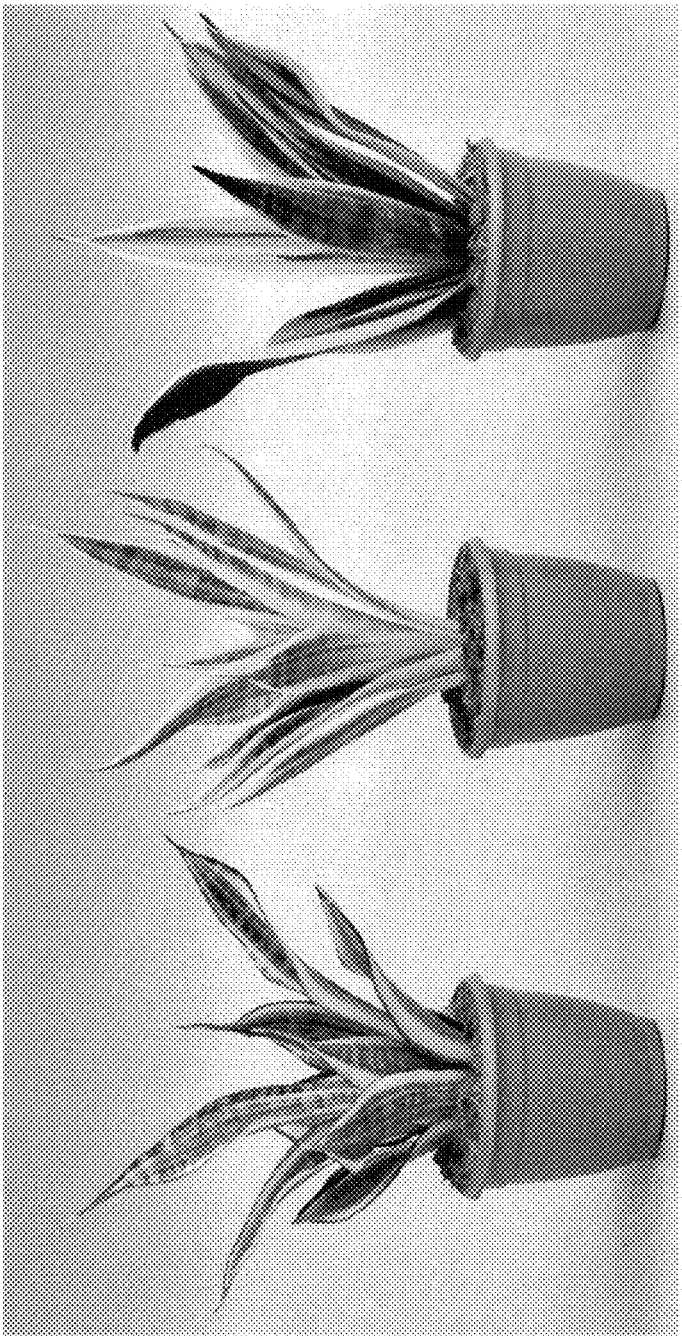

FIG. 7, FIG. 8 and FIG. 9: These three pictures show the three cultivars cited in this patent application together, photographed under same light conditions so visual comparisons are valid.

FIG. 7 shows the new cultivar Hansoti56 (Top) showing buttery yellowish-cream borders and light grey-green central band with occasional lines of cream and light green and showing subtle horizontal banding. The patented parent cultivar 'Hansoti23' (Bottom Left) showing broader leaves than Hansoti56 and more complex variegation pattern but still a relatively large number of leaves. Finally, the old, well-known cultivar 'Gold Flame' (Bottom Right) representing the classic "Compact *Sansevieria* Group" showing bigger, broader, more robust leaves and fewer leaves. The variegation pattern of the three cultivars, though all in the cream/yellowish/gold yellow range, is distinctly different from each other.

FIG. 8 Parent 'Hansoti23' (left), the new 'Hansoti56' (center) and 'Gold Flame' (right). Both, the parent 'Hansoti23' and the new cultivar 'Hansoti56' show a higher number of leaves per rosette compared to old standard "Compact *Sansevieria* Group" cultivars.

FIG. 9 illustrates the same three cultivars from a side view. Larger number of leaves per rosette, more vertical orientation and narrow but gracefully curving leaves of Hansoti56 (Center) are obvious.

Figure 10:
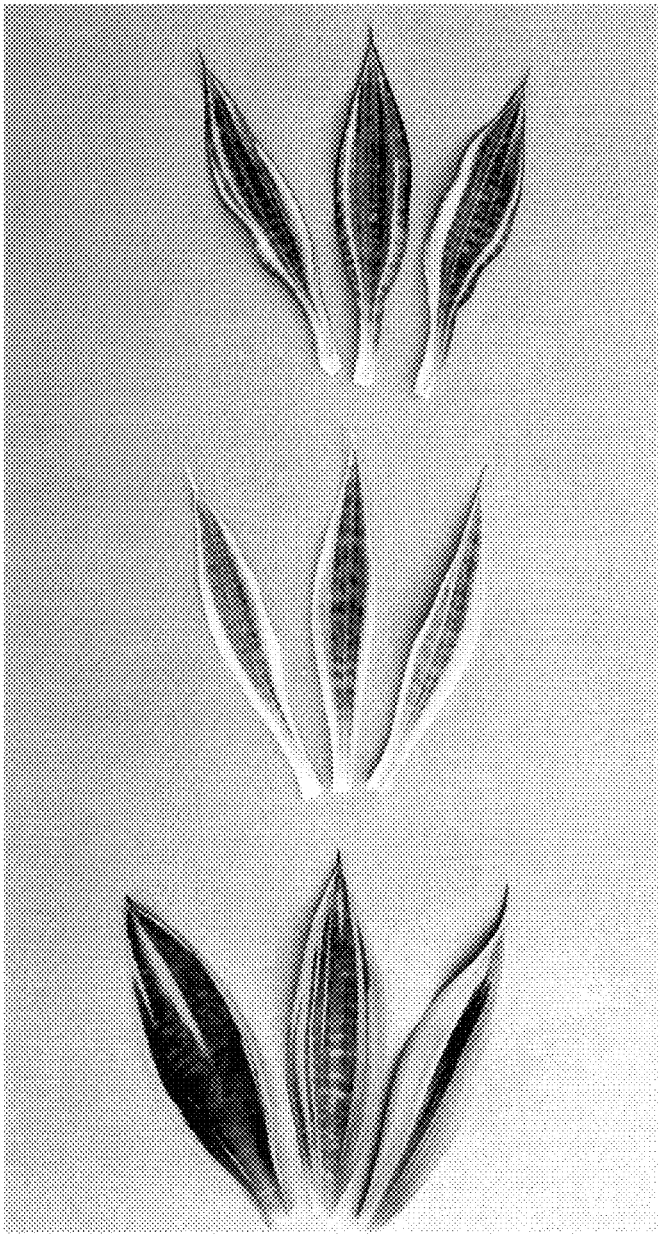
Figure 11:
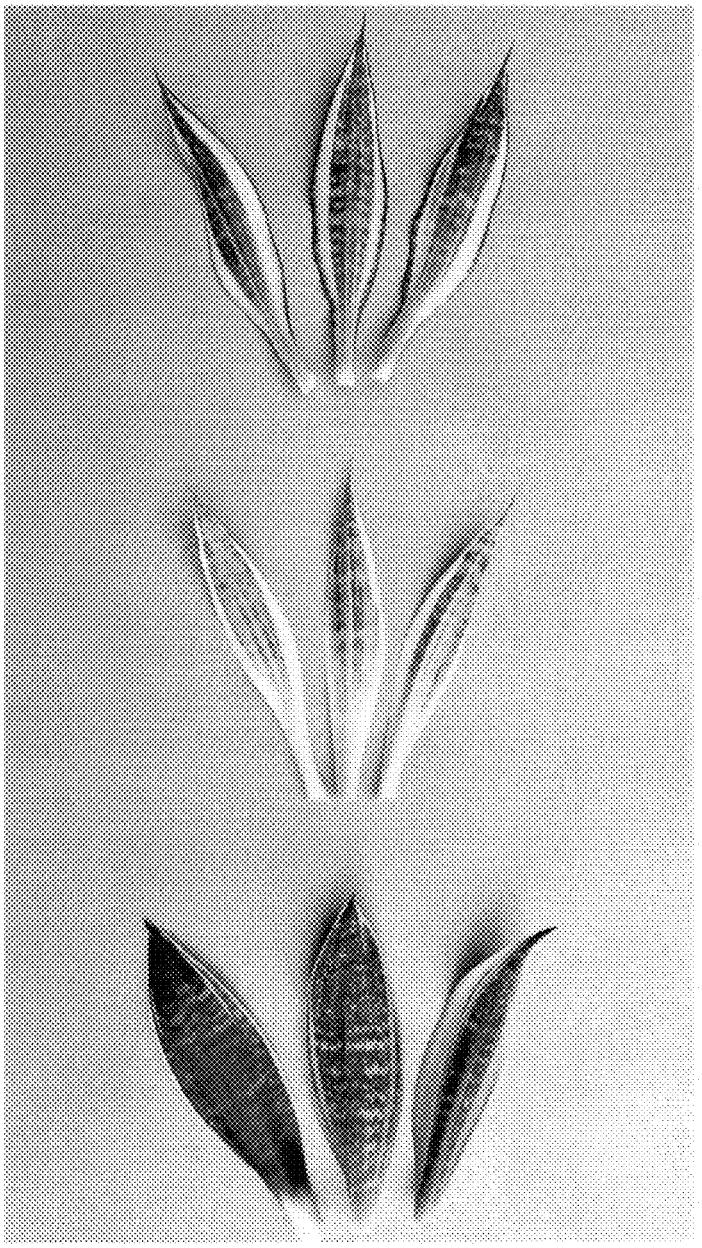

FIG. 10 shows individual leaves (adaxial surface view) of *Sansevieria* 'Hansoti56' (Centre), the parental patented variety 'Hansoti23' (Top row) and leaves of *Sansevieria* 'Gold Flame' (Bottom Row) shown together to show the differences in variegation pattern and colour. For 'Gold Flame' we present three leaves at different colour stages-leaves on young plants start out quite green and with age they lose the green colour to become more and more gold. Here the youngest leaf is on left and progressively older leaves to the right of that stack FIG. 11: shows the backside (abaxial surface) of the same individual leaves shown in FIG. 10.

DETAILED BOTANICAL DESCRIPTION

The new *Sansevieria* 'HANSOTI56' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI56' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer of 13:11:11 Type 360-days release at 1 kilo/cubic meter of media, constant liquid feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the winter season in Asle, District Satara, Maharashtra State, India when outdoor day temperature was 25° C. to 30° C. and cool nights, usually of 10° C. to 15° C. The age of the plants described is 3-4 months from rooted liners.

Botanical classification: *Sansevieria trifasciata* 'HANSOTI56'.

General information:

*Parentage.*—*Sansevieria trifasciata* 'Hansoti23', U.S. Plant Pat. No. 33,150.

*Optimal growth conditions.*—

*Light intensities.*—Good adaptability to outdoor (in tropical regions) or indoor conditions.

*Temperature.*—Day: 25° C. to 35° C. Night: 15° C. to 25° C.

*Temperature tolerance.*—Tolerant to a low temperature of about 8° C. and a high temperature of 38° C. and above-very heat tolerant.

*Fertilization.*—Constant feed of 100 ppm N, 30 ppm P and 100 ppm K is used along with micronutrients with occasional leaching.

*Growth regulators.*—Not necessary for growth, however rooting hormone aids in rapid and prolific rooting of offsets.

Propagation:

*Typical.*—Vegetative, by side suckers which come true to type. Does not come true from leaf cuttings.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots.*—25 to 30 days at 25°° C. to 30° C.

*Time to produce a rooted liner.*—About 45 to 50 days at 25° C. to 30° C.

*Time to produce ready* 12 *cm potted plant from liner.*—About 3 months at 25° C. to 30° C.

Plant:

*General appearance and form.*—Monocot; leaf bases arranged in a rosette around growth point.

*Height.*—About 25 to 30 cm when grown in 12 cm pots.

*Spread.*—About 20 to 25 cm when grown when grown in a 12 cm size container.

*Growth rate and habit.*—Medium growth rate compared to other similar *Sansevieria*; upright.

*Shape.*—Inverted triangle.

*Fragrance.*—None.

*Stem.*—Modified (rhizomes with erect foliage).

*Rosette height.*—About 25 to 30 cm height from top of pot when grown in 12 cm size container.

*Rosette diameter.*—About 15 to 20 cm.

*Texture.*—Smooth, waxy.

*Color.*—As described above.

*Strength.*—Strong and durable.

*Internode length.*—About 1 to 2 mm.

Foliage:

*Quantity.*—About 12 to 15 leaves at saleable stage or more with age.

*Arrangement and attachment.*—Single, alternate; leaf bases arranged stiffly in a rosette around central growth point.

*Leaf length.*—About 25 to 35 cm.

*Leaf width.*—About 4 cm.

*Overall shape of leaf.*—Lanceolate.

*Apex shape.*—Acute, triangular and aristate, with soft tip.

*Base shape.*—Plane.

*Margin.*—Sharp, smooth.

*Texture.*—Upper Surface: Smooth and waxy texture.

*Texture.*—Under Surface: Smooth and waxy texture.

*Pubescence.*—None.

*Color of mature leaf.*—Upper Surface: Basal cream colored border bands near 5A with dark central band varying from RHS Green 136A to lighter bands near Green N138C — exact shade difficult to pinpoint because overlying cream color tissue veils the central green band.

*Crossbanding.*—only on the central green band, as typical for many *Sansevieria* but somewhat less prominent.

*Venation pattern.*—Longitudinal/parallel.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs (*Rhizoecus pritchardi*). Typical pests include *Pseudococcidae longispinus* and *Tetranychus urticae.*

*Disease resistance.*—Occasionally shows *Anthracnose* and leaf spots but largely disease-free from clean mother stock and appropriate disease mitigation measures undertaken.

*Fruit/seed production.*—No fruits/seeds detected to date.

What is claimed is:

1. A new and distinct cultivar of *Sansevieria* plant named 'HANSOTI56' as herein illustrated and described.

* * * * *